US012755837B2

(12) United States Patent
Beckers et al.

(10) Patent No.: US 12,755,837 B2
(45) Date of Patent: Oct. 6, 2026

(54) METHOD FOR DETECTING RESPIRATORY EFFORT RELATED AROUSALS (RERA) THROUGH MODIFIED MANDIBULAR DISTANCE OR MOVEMENT SIGNALS IN SUBJECTS SUFFERING FROM SLEEP DISORDER

(71) Applicant: NOMICS, Angleur (BE)

(72) Inventors: Bernard Beckers, Angleur (BE); Pierre Ansay, Angleur (BE)

(73) Assignee: NOMICS, Angleur (BE)

( * ) Notice: Subject to any disclaimer, the term of this patent is extended or adjusted under 35 U.S.C. 154(b) by 0 days.

(21) Appl. No.: 18/716,331

(22) PCT Filed: Nov. 13, 2022

(86) PCT No.: PCT/EP2022/081690

§ 371 (c)(1),
(2) Date: Jun. 4, 2024

(87) PCT Pub. No.: WO2023/099172

PCT Pub. Date: Jun. 8, 2023

(65) Prior Publication Data

US 2024/0339212 A1 Oct. 10, 2024

(30) Foreign Application Priority Data

Dec. 5, 2021 (BE) .................................. 2021/5942

(51) Int. Cl.

| | |
|---|---|
| ***G16H 50/30*** | (2018.01) |
| ***A61B 5/00*** | (2006.01) |
| ***A61B 5/11*** | (2006.01) |
| ***A61B 5/113*** | (2006.01) |
| ***G16H 40/67*** | (2018.01) |

(52) U.S. Cl.
CPC ............ *G16H 40/67* (2018.01); *A61B 5/1114* (2013.01); *A61B 5/113* (2013.01); *A61B 5/4806* (2013.01); *G16H 50/30* (2018.01)

(58) Field of Classification Search
CPC ..... A61B 5/4806; A61B 5/0816; G16H 50/30
See application file for complete search history.

(56) References Cited

U.S. PATENT DOCUMENTS

| | | | | |
|---|---|---|---|---|
| 11,864,910 B2 * | 1/2024 | Martinot | .............. | A61B 5/7264 |
| 2007/0273366 A1 * | 11/2007 | Ansay | .................. | A61B 5/6822 600/26 |
| 2022/0330897 A1 * | 10/2022 | Martinot | .............. | A61B 5/6814 |

FOREIGN PATENT DOCUMENTS

| | | |
|---|---|---|
| EP | 3673802 A1 | 7/2020 |
| WO | 2020193778 A1 | 10/2020 |

OTHER PUBLICATIONS

Martinot JB, Senny F, Denison S, Cuthbert V, Gueulette E, Guénard H, Pépin JL. Mandibular movements identify respiratory effort in pediatric obstructive sleep apnea. J Clin Sleep Med. Apr. 15, 2015;11(5):567-74. doi: 10.5664/jcsm.4706. (Year: 2015).*

(Continued)

*Primary Examiner* — Evangeline Barr
(74) *Attorney, Agent, or Firm* — NIXON & VANDERHYE

(57) ABSTRACT

Methods, processes, storage media, apparatus and systems for method for detecting respiratory effort related arousals (RERA) through modified mandibular distance or movement signals in subjects suffering from sleep disorder are disclosed.

10 Claims, 7 Drawing Sheets

(56) References Cited

OTHER PUBLICATIONS

Senny F et al: "Midsagittal Jaw Movement Analysis for the Scoring of Sleep Apneas and Hypopneas", IEEE Transactions on Biomedical Engineering, IEEE, USA, vol. 55, No. 1, Jan. 1, 2008, pp. 87-95.

* cited by examiner

METHOD FOR DETECTING RESPIRATORY EFFORT RELATED AROUSALS (RERA) THROUGH MODIFIED MANDIBULAR DISTANCE OR MOVEMENT SIGNALS IN SUBJECTS SUFFERING FROM SLEEP DISORDER

FIELD OF THE DISCLOSURE

The present disclosure relates to methods, processes, storage media, apparatus and systems for method for detecting respiratory effort related arousals through modified mandibular distance or movement signals in subjects suffering from sleep disorder.

BACKGROUND

A mandibular distance measuring device has been described in WO2005071353. The distance or movement measuring device comprises an emitter and a receiver. The emitter is arranged to produce a magnetic field by means of a resonant circuit. The receiver picks up the resonant frequency of the emitter and converts the strength of the magnetic field into a signal. Devices of this type are for example available under the brand JAWAC® by Nomics SA in Liège Belgium.

An improvement of the mandibular distance measuring device of WO2005071353 is described in WO2020136259 also to Nomics SA. The sleep disorder detector comprises an emitter and a receiver. The emitter comprises an optimized energizing circuit, allowing very low power implementations and usage of a selected group of cables.

The JAWAC device may for example be used to regulate the respiratory devices, as described in WO2016041025 to Nomics SA.

However, it usually requires substantial experience to assess the mandibular distance signals obtained by the JAWAC® device.

Therefore, there is a need to provide improved methods of detecting sleep disorders, in particular to detect respiratory effort related arousals (RERA). It is a further objective of the invention to facilitate the assessment of the JAWA® signal.

Signal improvement in sleep disorders detectors has been described in WO200265901 to Ares Medical. It suggests to "smooth" the raw data in order to reduce the effects of noise and increase the detection of oxygen desaturation events. In this respect it suggests a smoothing algorithm for signals the oxygen saturation SpO2 from respiratory event monitoring in three successive steps using median filtering, slew limitation, and averaging by IIR filtering. However, it does not describe the modification of the mandibular distance or movement signal through averaging of the upper and the lower envelope Further, U.S. Pat. No. 8,192,376 inactive to Cardiac pacemakers describes a method for sleep state classification. However, it does not describe the modification of the mandibular distance or movement signal through averaging of the upper and the lower envelope of the signal. distance or movement signal.

Therefore, there remains a need to provide an improved method for detecting sleep disorders. In particular, there remains a need to provide biomarkers for the improved detection of respiratory-related arousals. Moreover, there remains a need to detect RERA and to distinguish them from non-respiratory sleep disorders and therefore allow for the appropriate treatment.

SUMMARY

One aspect of the present disclosure relates to a method for detecting respiratory effort related arousals through modified mandibular distance or movement signals obtained by a mandibular distance or movement measuring device in subjects suffering from sleep disorder. A further aspect of the invention is the provision of if improved mandibular distance or movement signals as biomarkers for the detection of respiratory-related arousals and their use for the detection of the onset of respiratory-related sleep disorders. The computer-implemented method may include:

- providing a mandibular distance or movement signal of a subject suffering from sleep disorders, wherein the mandibular distance or movement signal is being obtained by an electronic mandibular distance or movement measuring device;
- determining an average signal made of line or curve segments, in particular by
- determining the upper and the lower envelopes of the mandibular distance or movement signal of each respiratory cycle;
- averaging the upper and the lower envelopes of the mandibular distance to obtain an average signal;
- subtracting the average signal from the mandibular distance or movement signal to obtain a modified mandibular distance or movement signal;
- detecting the respiratory effort related arousal in the subject suffering from sleep disorders through the modified mandibular distance or movement signal.

In another aspect, the filtered mandibular signal is obtained by filtering a mandibular distance or movement signal with a linear phase, FIR, high-pass filter for example of length 400, for example with 0.095 Hz cut-off frequency, for example with a max 0.7 dB in-band ripple (above 0.15 Hz) or more than 75 dB attenuation below 0.015 Hz. Of course, other high-pass filtering options are available to the skilled person from the state of the art.

Another aspect of the present disclosure relates to a computer-readable storage medium for method for detecting respiratory effort related arousals (RERA) through modified mandibular distance or movement signals in subjects suffering from sleep disorder. In some embodiments, the computer-readable storage medium may include instructions being executable by one or more processors to perform the following steps:

- providing a mandibular distance or movement signal of a subject suffering from sleep disorders, wherein the mandibular distance or movement signal is being obtained by an electronic mandibular distance or movement measuring device;
- determining an average signal made of line or curve segments, in particular by
  - determining the upper and the lower envelopes of the mandibular distance or movement signal of each respiratory cycle;
  - averaging the upper and the lower envelopes of the mandibular distance to obtain an average signal;
- subtracting the average signal from the mandibular distance or movement signal to obtain a modified mandibular distance or movement signal;
- detecting the respiratory effort related arousal in the subject suffering from sleep disorders through the modified mandibular distance or movement signal.

Another aspect of the present disclosure relates to an apparatus configured for method for detecting respiratory effort related arousals (RERA) through modified mandibular distance or movement signals in subjects suffering from sleep disorder. In some aspects, the apparatus may include at least one memory storing computer program instructions and at least one processor configured to execute the computer program instructions to cause the apparatus at least to perform operations associated with method for detecting respiratory effort related arousals (RERA) through modified mandibular distance or movement signals in subjects suffering from sleep disorder. In some aspects, the computer program instructions may include

- providing a mandibular distance or movement signal of a subject suffering from sleep disorders, wherein the mandibular distance or movement signal is being obtained by an electronic mandibular distance or movement measuring device;
- determining an average signal made of line or curve segments, in particular by
  - determining the upper and the lower envelopes of the mandibular distance or movement signal of each respiratory cycle;
  - averaging the upper and the lower envelopes of the mandibular distance to obtain an average signal;
- subtracting the average signal from the mandibular distance or movement signal to obtain a modified mandibular distance or movement signal;
- detecting the respiratory effort related arousal in the subject suffering from sleep disorders through the modified mandibular distance or movement signal.

Another aspect of the present disclosure relates to a system for method for detecting respiratory effort related arousals through modified mandibular distance or movement signals in subjects suffering from sleep disorder. The system may include one or more hardware processors configured by machine-readable instructions for method for detecting respiratory effort related arousals through modified mandibular distance or movement signals in subjects suffering from sleep disorder. The machine-readable instructions may be configured to provide a mandibular distance or movement signal of a subject suffering from sleep disorders. The mandibular distance or movement signal may be obtained by an electronic mandibular distance or movement measuring device, the distance or movement measuring device comprises an emitter and a receiver and the emitter and the receiver may be configured to measure the distance of the mandible and a reference point on the face of the subject when placed on the mandible and the reference point. The machine-readable instructions may be configured to determine the upper and the lower envelopes of the mandibular distance or movement signal of each respiratory cycle. The machine-readable instructions may be configured to average the upper and the lower envelopes of the mandibular distance to obtain an average signal. The machine-readable instructions may be configured to subtract the average signal from the mandibular distance or movement signal to obtain a modified mandibular distance or movement signal. The machine-readable instructions may be configured to detect the respiratory effort related arousal in the subject suffering from sleep disorders through the modified mandibular distance or movement signal.

The modified mandibular distance or movement signal enables a facilitated and improvement assessment of the JAWAC® signal and in particular the detection of RERA as opposed to other sleep disorders.

DETAILED DESCRIPTION

Figure 1:
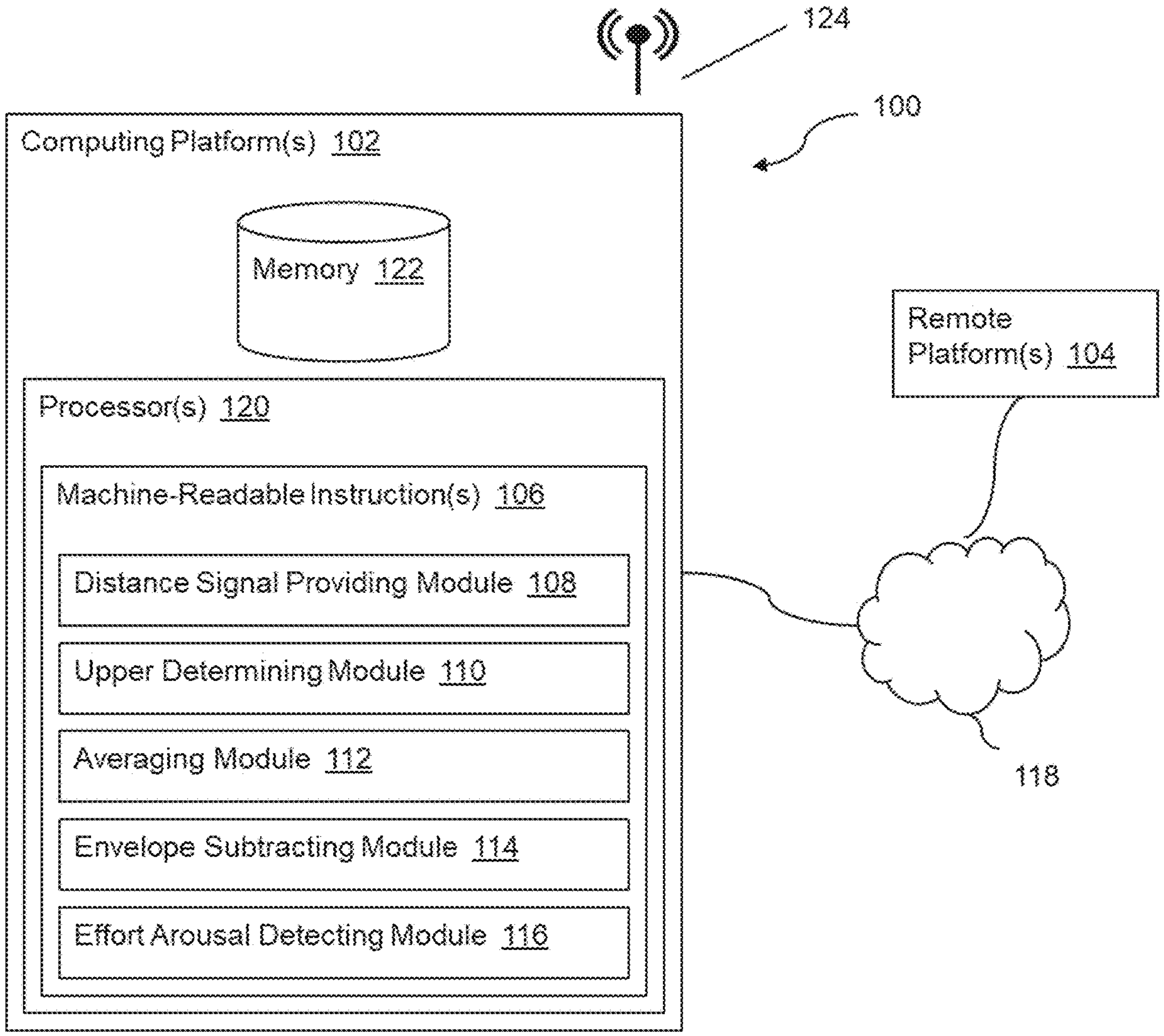
FIG. 1 illustrates a system configured for method for detecting respiratory effort related arousals (RERA) through modified mandibular distance or movement signals in subjects suffering from sleep disorder.

FIG. 1 illustrates a system configured for method for detecting respiratory effort related arousals (RERA) through modified mandibular distance or movement signals in subjects suffering from sleep disorder, in accordance with one or more embodiments. In some cases, system 100 may include one or more computing platforms 102. The one or more remote computing platforms 102 may be communicably coupled with one or more remote platforms 104. In some cases, users may access the system 100 via remote platform(s) 104.

The one or more computing platforms 102 may be configured by machine-readable instructions 106. Machine-readable instructions 106 may include modules. The modules may be implemented as one or more of functional logic, hardware logic, electronic circuitry, software modules, and the like. The modules may include one or more of distance or movement signal providing module 108, upper and lower envelope determining module 110, averaging module 112, envelope subtracting module 114, effort arousal detecting module 116, and/or other modules.

Distance or movement signal providing module 108 may be configured to provide a mandibular distance or movement signal of a subject suffering from sleep disorders. The mandibular distance or movement signal obtained by an electronic mandibular distance or movement measuring device, The distance or movement measuring device comprises an emitter and a receiver and The emitter and the receiver configured to measure the distance of the mandible and a reference point on the face of the subject when placed on the mandible and the reference point. Upper determining module 110 may be configured to determine the upper and the lower envelopes of the mandibular distance or movement signal of each respiratory cycle. Averaging module 112 may be configured to average the upper and the lower envelopes of the mandibular distance to obtain an average signal.

Envelope subtracting module 114 may be configured to subtract the average signal from the mandibular distance or movement signal to obtain a modified mandibular distance or movement signal. Effort arousal detecting module 116 may be configured to detect the respiratory effort related arousal in the subject suffering from sleep disorders through the modified mandibular distance or movement signal.

In some cases, the mandibular distance or movement signal may be a sinusoidal or oscillating signal.

In some cases, the averaging comprises determining the meeting points between the signal and the upper and the lower envelopes and the meeting points correspond to the extremes of a respiratory cycle; the upper envelopes may be obtained by the maximum amplitudes of the mandibular distance or movement signal and the lower envelopes may be obtained by the minimum amplitudes of the mandibular distance or movement signal.

In some cases, the average signal may be the sinusoidal or oscillating midline.

In some cases, the one or more computing platforms 102, may be communicatively coupled to the remote platform(s) 104. In some cases, the communicative coupling may include communicative coupling through a networked environment 118. The networked environment 118 may be a radio access network, such as LTE or 5G, a local area network (LAN), a wide area network (WAN) such as the Internet, or wireless LAN (WLAN), for example. It will be appreciated that this is not intended to be limiting, and that the scope of this disclosure includes implementations in which one or more computing platforms 102 and remote platform(s) 104 may be operatively linked via some other communication coupling. The one or more computing platforms 102 may be configured to communicate with the networked environment 118 via wireless or wired connections. In addition, in an embodiment, the one or more computing platforms 102 may be configured to communicate directly with each other via wireless or wired connections. Examples of one or more computing platforms 102 may include, but is not limited to, smartphones, wearable devices, tablets, laptop computers, desktop computers, Internet of Things (IoT) device, or other mobile or stationary devices. In an embodiment, system 100 may also include one or more hosts or servers, such as the one or more remote platforms 104 connected to the networked environment 118 through wireless or wired connections. According to one embodiment, remote platforms 104 may be implemented in or function as base stations (which may also be referred to as Node Bs or evolved Node Bs (eNBs)). In other embodiments, remote platforms 104 may include web servers, mail servers, application servers, etc. According to certain embodiments, remote platforms 104 may be standalone servers, networked servers, or an array of servers.

The one or more computing platforms 102 may include one or more processors 120 for processing information and executing instructions or operations. One or more processors 120 may be any type of general or specific purpose processor. In some cases, multiple processors 120 may be utilized according to other embodiments. In fact, the one or more processors 120 may include one or more of general-purpose computers, special purpose computers, microprocessors, digital signal processors (DSPs), field-programmable gate arrays (FPGAs), application-specific integrated circuits (ASICs), and processors based on a multi-core processor architecture, as examples. In some cases, the one or more processors 120 may be remote from the one or more computing platforms 102, such as disposed within a remote platform like the one or more remote platforms 120 of FIG. 1.

The one or more processors 120 may perform functions associated with the operation of system 100 which may include, for example, precoding of antenna gain/phase parameters, encoding and decoding of individual bits forming a communication message, formatting of information, and overall control of the one or more computing platforms 102, including processes related to management of communication resources.

The one or more computing platforms 102 may further include or be coupled to a memory 122 (internal or external), which may be coupled to one or more processors 120, for storing information and instructions that may be executed by one or more processors 120. Memory 122 may be one or more memories and of any type suitable to the local application environment, and may be implemented using any suitable volatile or nonvolatile data storage technology such as a semiconductor-based memory device, a magnetic memory device and system, an optical memory device and system, fixed memory, and removable memory. For example, memory 122 can consist of any combination of random access memory (RAM), read only memory (ROM), static storage such as a magnetic or optical disk, hard disk drive (HDD), solid state drive (SSD), or any other type of non-transitory machine or computer readable media. The instructions stored in memory 122 may include program instructions or computer program code that, when executed by one or more processors 120, enable the one or more computing platforms 102 to perform tasks as described herein.

In some embodiments, one or more computing platforms 102 may also include or be coupled to one or more antennas 124 for transmitting and receiving signals and/or data to and from one or more computing platforms 102. The one or more antennas may be configured to communicate via, for example, a plurality of radio interfaces that may be coupled to the one or more antennas. The radio interfaces may correspond to a plurality of radio access technologies including one or more of LTE, 5G, WLAN, Bluetooth, near field communication (NFC), radio frequency identifier (RFID), ultrawideband (UWB), and the like. The radio interface may include components, such as filters, converters (for example, digital-to-analog converters and the like), mappers, a Fast Fourier Transform (FFT) module, and the like, to generate symbols for a transmission via one or more downlinks and to receive symbols (for example, via an uplink).

Figure 2:
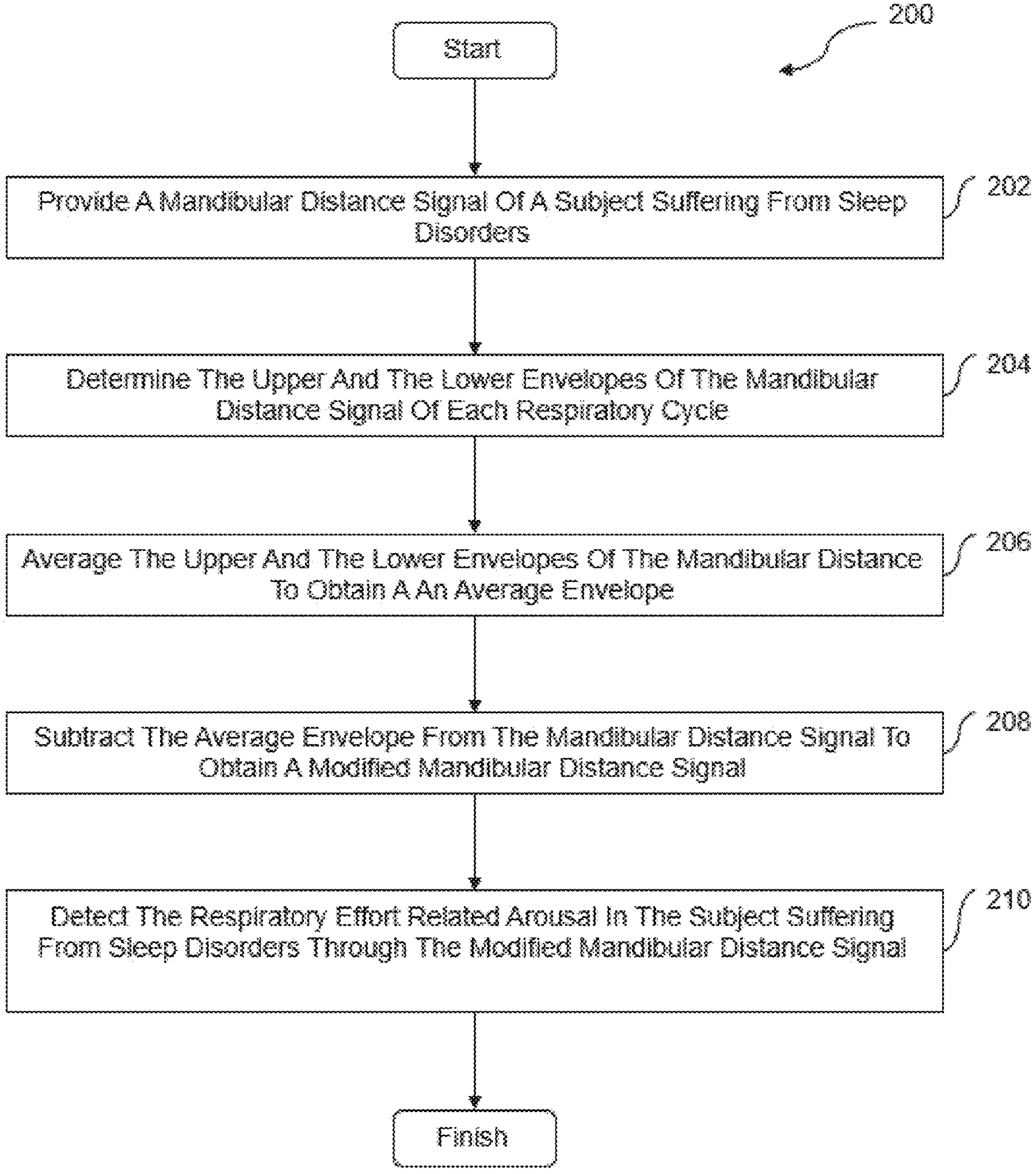
FIG. 2 illustrates a method for detecting respiratory effort related arousals (RERA) through modified mandibular distance or movement signals in subjects suffering from sleep disorder.

FIG. 2 illustrates an example flow diagram of a method 200, according to one embodiment. The method 200 may include providing a mandibular distance or movement signal of a subject suffering from sleep disorders at block 202, the mandibular distance or movement signal being obtained by an electronic mandibular distance or movement measuring device, the distance or movement measuring device comprises an emitter and a receiver and the emitter and the receiver being configured to measure the distance of the mandible and a reference point on the face of the subject when placed on the mandible and the reference point. The method 200 may include determining the upper and the lower envelopes of respiratory cycles in the mandibular distance or movement signal at block 204. The method 200 may include averaging the upper and the lower envelopes of the mandibular distance to obtain an average signal at block 206. The method 200 may include subtracting the average signal from the mandibular distance or movement signal to obtain a modified mandibular distance or movement signal at block 208. The method 200 may include detecting the respiratory effort related arousal in the subject suffering from sleep disorders through the modified mandibular distance or movement signal at block 210.

In some cases, the method 200 may be performed by one or more hardware processors, such as the processors 120 of FIG. 1, configured by machine-readable instructions, such as the machine-readable instructions 106 of FIG. 1. In this aspect, the method 200 may be configured to be implemented by the modules, such as the modules 108, 110, 112, 114 and/or 116 discussed above in FIG. 1.

Figure 3:
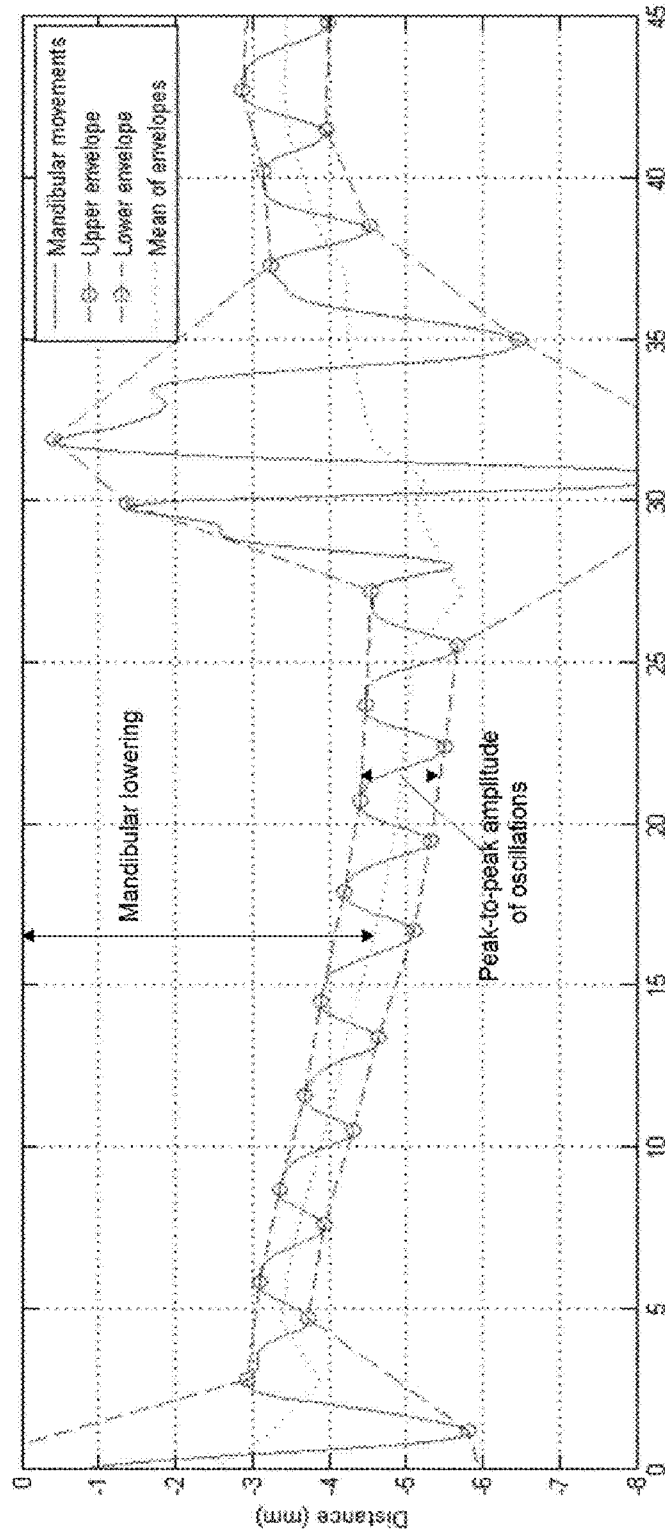
FIG. 3 illustrates a method for detecting respiratory effort related arousals (RERA) through modified mandibular distance or movement signals in subjects suffering from sleep disorder.

FIG. 3 shows a representative mandibular distance or movement signal recorded during 45 seconds of sleep of a subject suffering from the sleep disorder using the Jawac® mandibular distance device commercially available from Nomics SA in Belgium. The distance is expressed as mm on the vertical axis. The time is indicated on the horizontal axis. The black permanent line represents the oscillary mandibular movements during 45 seconds. The movements vary between 0 mm and around-8 mm which was observed at 30 seconds. The upper envelope is represented by the red line. The lower envelope is represented by the green line.

Figure 4:
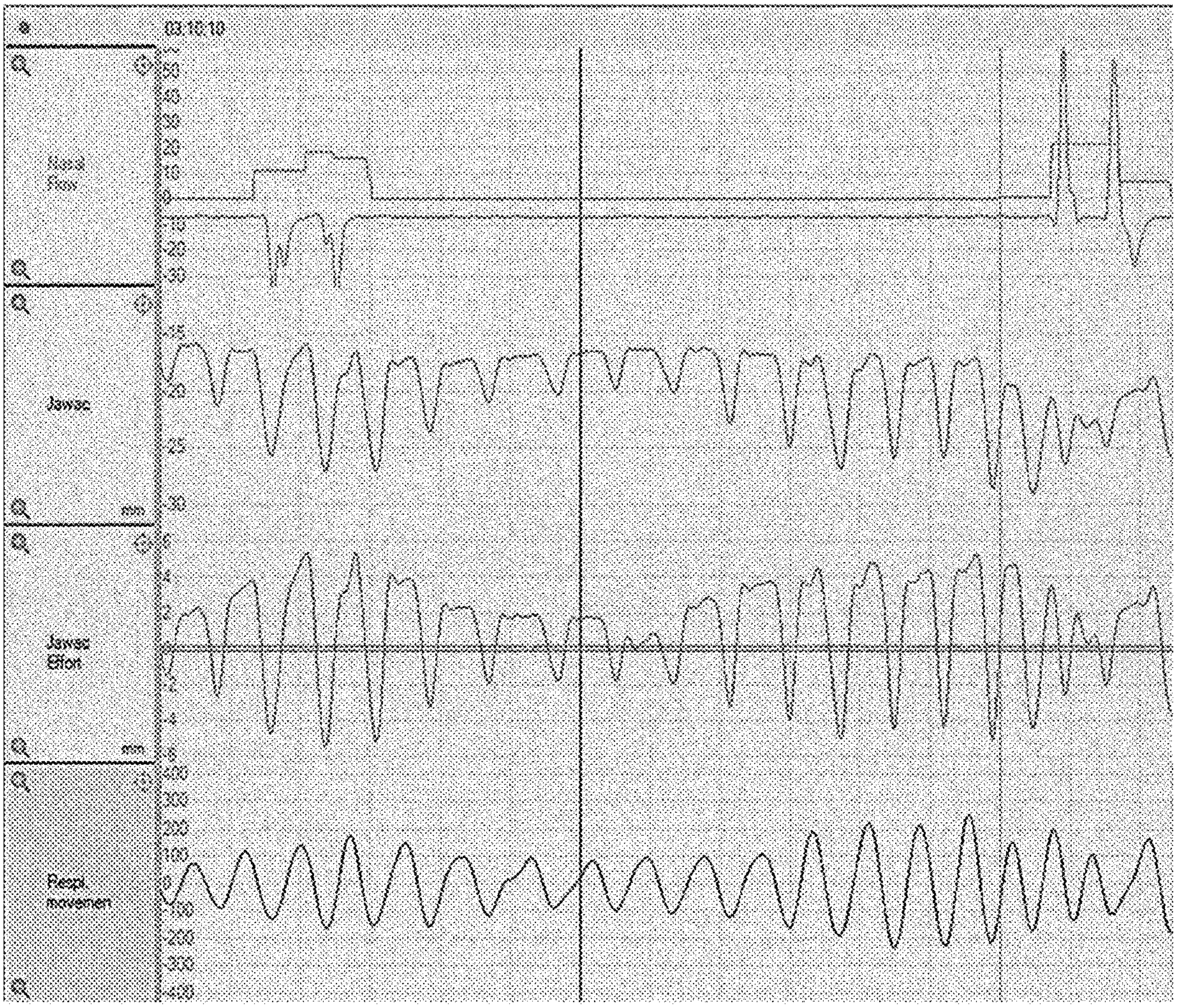
FIG. 4 illustrates the method of the present invention (Jawac effort) compared to the state of the art (Jawac) in a subject that shows an obstruction through RERA.

FIG. 4 shows an exemplary modified mandibular distance or movement signal referred to as Jawac Effort. It also shows the mandibular distance or movement signal referred to as Jawac, as well as the nasal flow and the respiratory movement.

Following examples are for illustration purposes and are in no way meant to be limiting.

EXAMPLES

Example 1 includes a method comprising: providing a mandibular distance or movement signal of a subject suffering from sleep disorders, determining the upper and the lower envelopes of the mandibular distance or movement signal of each respiratory cycle, averaging the upper and the lower envelopes of the mandibular distance to obtain a an average signal, subtracting the average signal from the mandibular distance or movement signal to obtain a modified mandibular distance or movement signal and detecting the respiratory effort related arousal in the subject suffering from sleep disorders through the modified mandibular distance or movement signal.

Example 2 includes the method of example(s) 1 and/or some other example(s) herein, wherein the mandibular distance or movement signal is a sinusoidal or oscillating signal.

Example 3 includes the method of example(s) 1 and/or some other example(s) herein, wherein the upper envelopes are obtained through interpolating maximum amplitudes of a distance of 10 seconds or more, preferably 20 seconds or more, even more preferably 25 seconds or more.

Example 4 includes the method of example(s) 1 and/or some other example(s) herein, wherein the upper envelopes are obtained through interpolating maximum amplitudes of a distance of 50 seconds or more, preferably 50 seconds or more, even more preferably 10 seconds or more.

Example 5 includes the method of example(s) 1 and/or some other example(s) herein, wherein the averaging comprises determining the meeting points between the signal and the upper and the lower envelopes and the meeting points correspond to the extremes of a respiratory cycle.

Example 6 includes the method of example(s) 1 and/or some other example(s) herein, wherein the upper envelopes are obtained by the maximum amplitudes of the mandibular distance or movement signal.

Example 7 includes the method of example(s) 1 and/or some other example(s) herein, wherein the lower envelopes are obtained by the minimum amplitudes of the mandibular distance or movement signal.

Example 8 includes the method of example(s) 1 and/or some other example(s) herein, wherein the average signal is the sinusoidal or oscillating signal midline.

Example 9 includes the method of example(s) 1 and/or some other example(s) herein, wherein the upper and lower envelopes are obtained during a time of 1 second or more, preferably, during a time of 1.5 seconds or more, and even more preferably during 5 seconds or more.

Example 10 includes the method of example(s) 1 and/or some other example(s) herein, wherein the upper and lower envelopes are obtained by the maximum and minimum amplitudes of the mandibular distance or movement signal during a time of 15 seconds or less, preferably, during a time of 10 seconds or less, and even more preferably during 5 seconds or less.

Example 11 includes the method of example(s) 1 and/or some other example(s) herein, wherein the relating to the presence or the absence of respiratory effort related arousals.

Example 12 includes a storage medium comprising: providing a mandibular distance or movement signal of a subject suffering from sleep disorders, determining the upper and the lower envelopes of the mandibular distance or movement signal of each respiratory cycle, averaging the upper and the lower envelopes of the mandibular distance to obtain a an average signal, subtracting the average signal from the mandibular distance or movement signal to obtain a modified mandibular distance or movement signal and detecting the respiratory effort related arousal in the subject suffering from sleep disorders through the modified mandibular distance or movement signal.

Example 13 includes a system comprising: providing a mandibular distance or movement signal of a subject suffering from sleep disorders, determining the upper and the lower envelopes of the mandibular distance or movement signal of each respiratory cycle, averaging the upper and the lower envelopes of the mandibular distance to obtain a an average signal, subtracting the average signal from the mandibular distance or movement signal to obtain a modified mandibular distance or movement signal and detecting the respiratory effort related arousal in the subject suffering from sleep disorders through the modified mandibular distance or movement signal.

Figure 5:
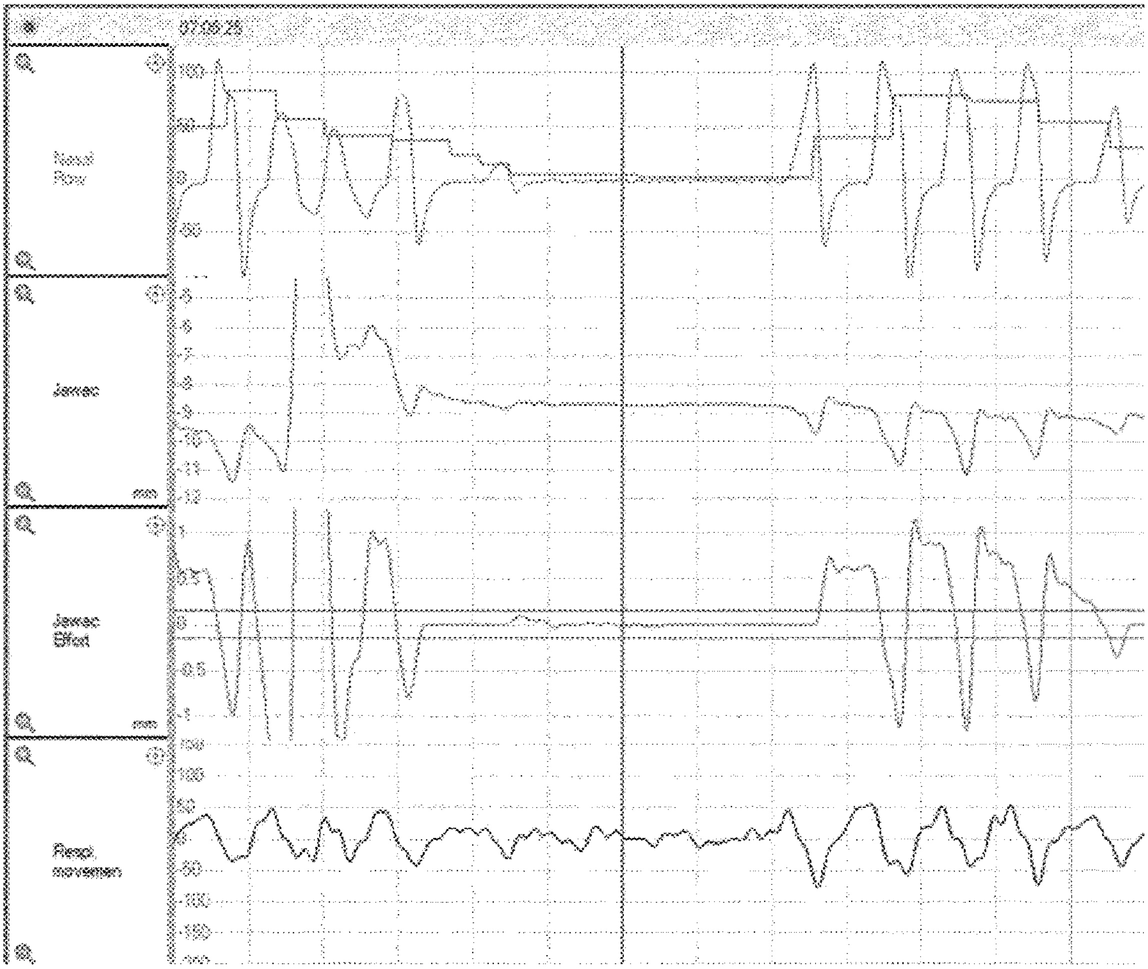
FIG. 5 illustrates the method of the present invention (Jawac effort) compared to the state of the art (Jawac) in a subject that shows no RERA.
Figure 6:
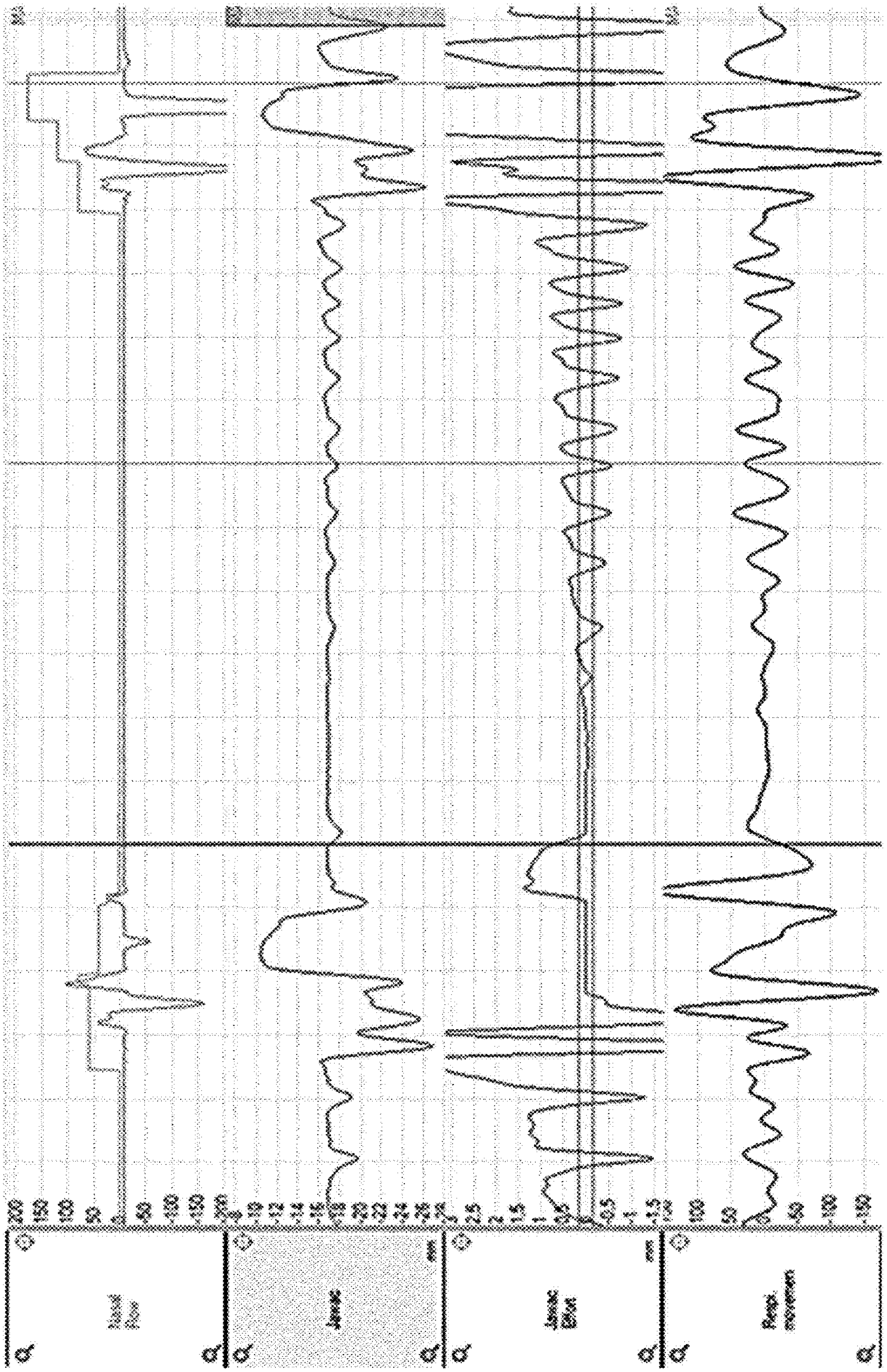
FIG. 6 illustrates the method of the present invention (Jawac effort) compared to the state of the art (Jawac) in a subject that shows no RERA and then RERA resulting in a mixed signal.

Example 14 shows an exemplary embodiment with a signal of a RERA signal (FIG. 4), a neutral signal without effort (FIG. 5) and a mixed signal (FIG. 6).

FIG. 5 illustrates the method of the present invention (Jawac effort) compared to the state of the art (Jawac) in a subject that shows no RERA.

FIG. 6 illustrates the method of the present invention (Jawac effort) compared to the state of the art (Jawac) in a subject that shows no RERA and then RERA resulting in a mixed signal.

Figure 7:
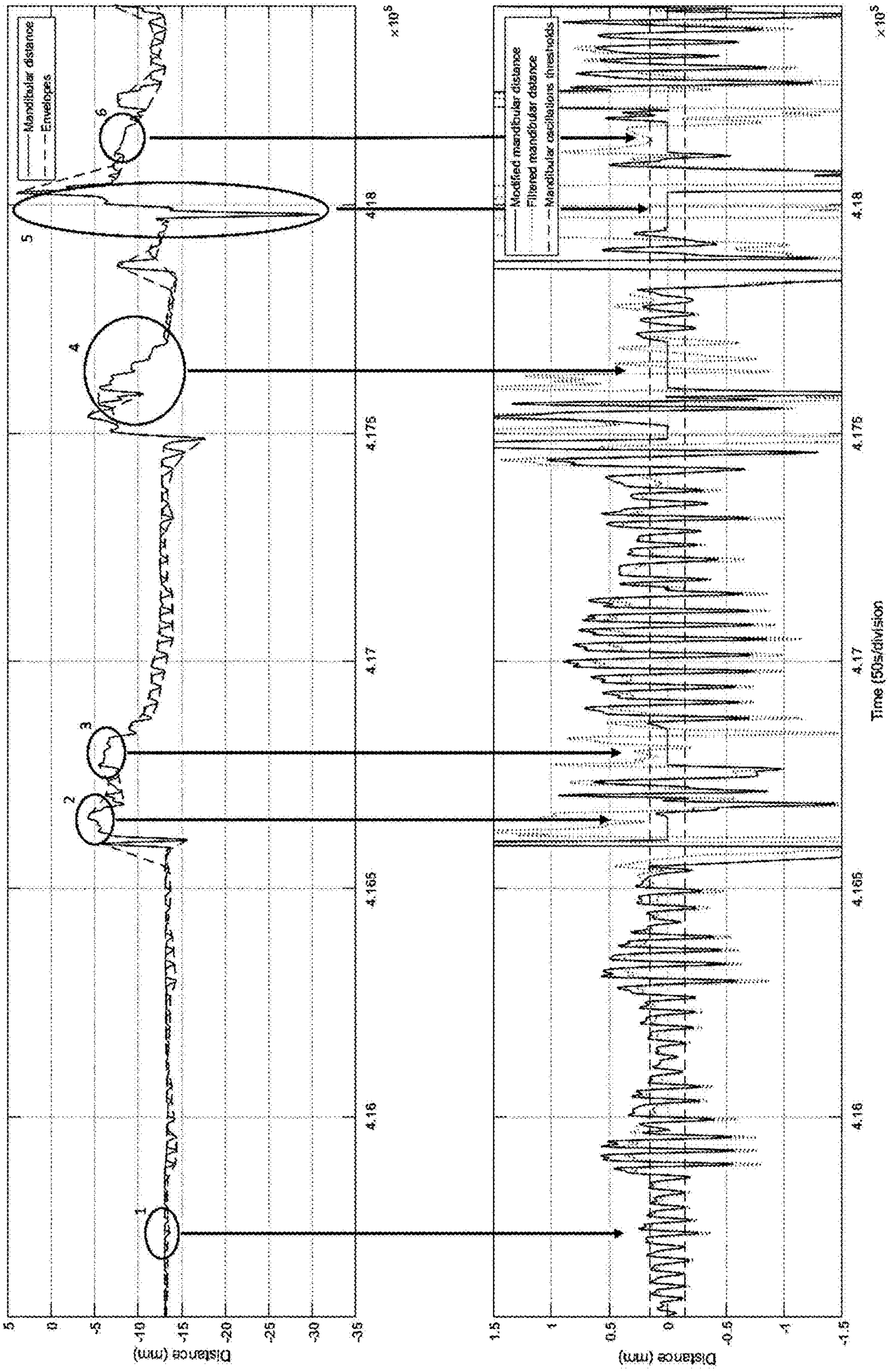
FIG. 7 illustrates the method of the present invention (Jawac effort) compared to the state of the art in a subject that shows no RERA and then RERA resulting in a mixed signal.

FIG. 7 illustrates the method of the present invention (Jawac effort) compared to the state of the art (Jawac) in a subject that shows no RERA and then RERA resulting in a mixed signal. In this embodiment, the filtered mandibular signal is obtained by filtering the Jawac signal with a linear phase, FIR, high-pass filter of length 400, with 0.095 Hz cut-off frequency, max 0.7 dB in-band ripple (above 0.15 Hz) and more than 75 dB attenuation below 0.015 Hz. Of course, other high-pass filtering options are available to the skilled person from the state of the art. Examples of sections where modified mandibular signal outperforms filtered mandibular signals are marked as follows:

Section 1: avoiding false detection of arousals (presence of a spike);

Section 2 and 3: avoiding confusion of wake signals with breathing effort;

Section 4 and 6: avoiding false detection of breathing effort; and

Section 5: avoiding confusion of arousal and breathing effort.

Translation Table of Expressions in the Figures:

| |
|---|
| Computing Platform |
| Memory |
| Processor |
| Machine-Readable Instructions |
| Distance or movement signal Providing Module |
| Upper Determining Module |
| Averaging Module |
| Envelope Subtracting Module |
| Effort Arousal Detecting Module |
| Remote Platform |
| Start |
| Provide A Mandibular Distance or movement signal Of A Subject Suffering From Sleep Disorders |
| Determine The Upper And The Lower Envelopes Of The Mandibular Distance or movement signal Of Each Respiratory Cycle |
| Average The Upper And The Lower Envelopes Of The Mandibular Distance To Obtain A An Average signal |
| Subtract The Average signal From The Mandibular Distance or movement signal To Obtain A Modified Mandibular Distance or movement signal |
| Detect The Respiratory Effort Related Arousal In The Subject Suffering From Sleep Disorders Through The Modified Mandibular Distance or movement signal |
| Finish |
| Mandibular lowering |
| Peak-to-peak amplitude of oscillations |
| Time |
| Distance |
| Nasal Flow |
| Jawac |
| Jawac Effort |
| Resp. movement |
| Division |

The invention claimed is:

1. A computer-implemented method, comprising:

producing a magnetic field using a resonant circuit emitter;

providing a receiver;

measuring, using the resonant circuit emitter and the receiver, a mandible and a reference point on a face of a subject to obtain a mandibular distance or movement signal of the subject suffering from sleep disorders;

determining an average signal made of line or curve segments, by determining the upper and the lower envelopes of the mandibular distance or movement signal of each respiratory cycle, the upper envelopes being obtained by the maximum amplitudes of the mandibular distance or movement signal, the lower envelopes being obtained by the minimum amplitudes of the mandibular distance or movement signal, and averaging the upper and the lower envelopes of the mandibular distance to obtain the average signal;

subtracting the average signal from the mandibular distance or movement signal to obtain a modified mandibular distance or movement signal; and detecting a respiratory effort related arousal in the subject suffering from sleep disorders through the modified mandibular distance or movement signal.

2. The computer-implemented method of claim 1, wherein the modified mandibular distance or movement signal is computed only during valid respiratory cycles, wherein valid respiratory cycles are defined as oscillations having a frequency lower than 1 Hz and higher than 0.1 Hz.

3. The computer-implemented method of claim 1, wherein the modified mandibular distance or movement signal is set to values or displayed in a way that indicates the non-respiratory nature during invalid respiratory cycles.

4. The computer-implemented method of claim 1, wherein the averaging comprises determining the meeting points between the signal and the upper and the lower envelopes, wherein the meeting points correspond to the extremes of a respiratory cycle.

5. The computer-implemented method of claim 1, wherein the average signal is the sinusoidal or oscillating midline.

6. The computer-implemented method of claim 1, wherein the modified mandibular distance or movement signal is computed only during valid respiratory cycles, wherein valid respiratory cycles are defined as oscillations having a frequency lower than 0.5 Hz, and higher than 0.1 Hz.

7. The computer-implemented method of claim 1, wherein the modified mandibular distance or movement signal is computed only during valid respiratory cycles, wherein valid respiratory cycles are defined as oscillations having a frequency lower than 1 Hz and higher than 0.15 Hz.

8. The computer-implemented method of claim 1, wherein the modified mandibular distance or movement signal is computed only during valid respiratory cycles, wherein valid respiratory cycles are defined as oscillations having a frequency lower than 0.5 Hz, and higher than 0.15 Hz.

9. An apparatus, comprising:

at least one memory storing computer program instructions; and at least one processor configured to execute the computer program instructions to cause the apparatus at least to:

produce a magnetic field using a resonant circuit emitter, provide a receiver, measure, using the resonant circuit emitter and the receiver, a mandible and a reference point on a face of a subject to obtain a mandibular distance or movement signal of the subject suffering from sleep disorders, determine an average signal made of line or curve segments by determining the upper and the lower envelopes of the mandibular distance or movement signal of each respiratory cycle, the upper envelopes being obtained by the maximum amplitudes of the mandibular distance or movement signal, the lower envelopes being obtained by the minimum amplitudes of the mandibular distance or movement signal, and averaging the upper and the lower envelopes of the mandibular distance to obtain the average signal, subtract the average signal from the mandibular distance or movement signal to obtain a modified mandibular distance or movement signal, and detect a respiratory effort related arousal in the subject suffering from sleep disorders through the modified mandibular distance or movement signal.

10. A system, comprising:

one or more hardware processors configured by machine-readable instructions to:

produce a magnetic field using a resonant circuit emitter, provide a receiver, measure, using the resonant circuit emitter and the receiver, a mandible and a reference point on a face of a subject to obtain a mandibular distance or movement signal of the subject suffering from sleep disorders, determine an average signal made of line or curve segments by determining the upper and the lower envelopes of the mandibular distance or movement signal of each respiratory cycle, the upper envelopes being obtained by the maximum amplitudes of the mandibular distance or movement signal, the lower envelopes being obtained by the minimum amplitudes of the mandibular distance or movement signal, and averaging the upper and the lower envelopes of the mandibular distance to obtain an average signal, subtract the average signal from the mandibular distance or movement signal to obtain a modified mandibular distance or movement signal, and detect a respiratory effort related arousal in the subject suffering from sleep disorders through the modified mandibular distance or movement signal.

* * * * *